(12) United States Patent
Kubler-Kielb et al.

(10) Patent No.: US 7,422,755 B2
(45) Date of Patent: Sep. 9, 2008

(54) ANTIMULTIORGANISM GLYCOCONJUGATE VACCINE

(75) Inventors: Joanna Kubler-Kielb, Rockville, MD (US); Rachel Schneerson, Bethesda, MD (US); John B. Robbins, Chevy Chase, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 233 days.

(21) Appl. No.: 11/035,884

(22) Filed: Jan. 18, 2005

(65) Prior Publication Data

US 2005/0158346 A1 Jul. 21, 2005

Related U.S. Application Data

(60) Provisional application No. 60/536,497, filed on Jan. 15, 2004.

(51) Int. Cl.
*A61K 45/00* (2006.01)
*A61K 39/00* (2006.01)
*C12P 19/00* (2006.01)
*C07K 1/00* (2006.01)
*C07K 16/00* (2006.01)

(52) U.S. Cl. .................. 424/278.1; 435/72; 424/184.1; 530/350; 530/388.1

(58) Field of Classification Search .............. 424/124.1, 424/181.1, 278.1, 184.1; 530/350, 388.1; 435/72

See application file for complete search history.

(56) References Cited

U.S. PATENT DOCUMENTS

| | | | | |
|---|---|---|---|---|
| 4,356,170 A | * | 10/1982 | Jennings et al. | 424/194.1 |
| 4,644,059 A | * | 2/1987 | Gordon | 536/117 |
| 5,306,492 A | * | 4/1994 | Porro | 424/194.1 |
| 2002/0119166 A1 | * | 8/2002 | Pier et al. | 424/234.1 |
| 2004/0213804 A1 | * | 10/2004 | Michon et al. | 424/190.1 |

OTHER PUBLICATIONS

Archibald et al (The glycerol teichoic acid from walls of *Staphylococcus epidermidis* 12, Biochem. J., 1968; 110: 583-588).*
Pozsgay et al (Protein conjugates of synthetic saccharides elicit higher levels of serum IgG lipopolysaccharide antibodies in mice than do those of O-specific polysaccharide from *Shigella dysenteriae* type 1, Proc. Natl. Acad. Sci. USA, 1999; 96: 5194-97).*
Myerowitz et al (Polysaccharides of the genus *Bacillus* cross-reactive with the capsular polysaccharides of *Diplococcus pneumoniae* Type III, *Haemophilus influenzae* Type b and *Neisseria meningitidis* Group A, Infection and Immunity, 1973; 8(6): 896-900).*
Greenspan et al. (Nature Biotechnology 17: 936-937, 1999).*
Myerowitz et al. (1973), Polysaccharides of the Genus *Bacillus* Cross-Reactive with the Capsular Polysaccharides of *Diplococcus pneumoniae* Type III, *Haemophilus influenzae* Type b, and *Neisseria meningitides* Group A, Infection and Immunity 8, 896-900.
Argaman et al. (1974), Polyribitol-Phosphate: An Antigen for Four Gram-Positive Bacteria Cross-Reactive with the Capsular Polysaccharide of *Haemophilus influenzae* Type B, *J. Immunol.* 112, 649-655.
Bradshaw et al. (1971), Bacterial Antigens Cross-Reactive with the Capsular Polysaccharide of *Haemophilus influenzae* Type b, The Lancet 1(7709), 1095-1096.
Pozsgay et al. (1999) Protein conjugates of synthetic saccharides elicit higher levels of serum IgG lipopolysaccharide antibodies in mice than do those of the O-specific polysaccharide from *Shigella dysenteriate* type 1,*Proc Natl Acad Sci USA* 96, 5194-5197.
Schneerson et al. (2003) Poly (v-D-glutamic acid) protein conjugates induce IgG antibodies in mice to the capsule of *Bacillus anthracis*: A potential addition to the anthrax vaccine, *Proc Natl Acad Sci USA* 100, 8945-8950.
Kubler-Kielb et al. (2004) Chemical Structure, Conjugation, and Cross-Reactivity of *Bacillus pumilus* Sh18 Cell Wall Polysaccharide, *J Bacteriol*, 186, 6891-6901).
Zielen et al. (1996), Simple determination of polysaccharide specific antibodies by means of chemically modified ELISA plates, *J. Immunol Methods*, 193, 1-7.
Archibald et al. (1966), The Teichoic Acids, *Adv Carbohydr Chem Biochem*. 21, 323-75.
Naumova et al. (1997), Anionic Polymers in Cell Walls of Gram-Positive Bacteria, *Biochemistry* (Mosc). 62, 809-40.
Sutton et al. (1985), An Avidin-Biotin Based ELISA for Quantitation of Antibody to Bacterial Polysaccharides, *J Immunol Methods* 82, 215-24.
Myerowitz et al. (1973), Induction of *Haemophilius influenzae* Type b Capsular Antibody in Neonatal Rabbits by Gastrointestinal Colonization with Cross-Reacting *Escherichia coli*, *Infection and Immunity* 7, 137-140.
Kojima et al.(1985), Structure of the Linkage Unites Between Ribitol Teichoic Acids and Peptidoglycan, *J Bacteriol*, 161, 299-306).
Kojima et al.(1985), Structural studies on the linkage unit between (N-acetylglucosamine 1-phosphate) and peptidoglycan in cell walls of *Bacillus pumilus* AHU 1650, *Eur J Bacteriol*. 149, 331-336.

* cited by examiner

*Primary Examiner*—Robert A Zeman
*Assistant Examiner*—Lakia J Tongue
(74) *Attorney, Agent, or Firm*—Nancy J. Axelrod; Thomas G. Wiseman; Venable LLP

(57) ABSTRACT

The present invention relates, e.g., to a glycoconjugate composition comprising one or more polysaccharide types from a cell wall polysaccharide preparation from *B. pumilus* Sh 18, or variants thereof. Also disclosed are antibodies generated against the glycoconjugates, and methods of using the glycoconjugates and antibodies. An antimultiorganism vaccine which reacts against at least *Haemophilus influenzae* type a, *Haemophilus influenzae* type b, *Staphylococcus aureus*, and *Staphylococcus epidermidis*, is disclosed.

5 Claims, 6 Drawing Sheets

*H. influenzae* type b CP
(Lemercinier *et al.* (2000)
*Biologicals* 28, 175-83)

*H. influenzae* type a CP
(Branefors-Helander (1977)
*Carbohydr Res* 56, 117-22)

*S. aureus* CWP
(Baddily *et al.* (1962)
*Biochem J.* 82, 439-448)

*S. epidermidis* CWP
(Endl *et al.* (1984)
*Arch Microbiol.* 137, 272-80)

*B. pumilus* Sh17 CWP
(Vann *et al.* (1976)
*Infect Immun* 13, 1654-62)

*B. pumilus* Sh18 CWP (PROPOSED STRUCTURES)

US 7,422,755 B2

ANTIMULTIORGANISM GLYCOCONJUGATE VACCINE

This application claims the benefit of the filing date of U.S. Provisional application Ser. No. 60/536,497, filed Jan. 15, 2004, which is incorporated by reference herein in its entirety.

FIELD OF THE INVENTION

This invention relates, e.g., to a cell wall polysaccharide preparation from a bacterium; glycoconjugates thereof; treatment methods using the glycoconjugates; and compositions, including immunogenic compositions and vaccines.

BACKGROUND INFORMATION

Bacterial pathogens are responsible for variety of diseases worldwide. Among these pathogens are *Haemophilus influenza* type a ("Hia"), *Haemophilus influenza* type b ("Hib"), *Staphylococcus aureus* ("S. aureus") and *Staphylococcus epidermidis* ("S. epidermidis"). *H. influenza* type a has been reported to cause infections in Africa (Wall et al. (1986), *Bull World Health Organ* 64, 553-8; Wall et al. (1985), *Lancet* 845) and other countries (Rutherford et al. (1984), *Ped Inf Dis* 3, 575-77). *Haemophilus influenza* type b causes serious diseases, including mental retardation, which have the highest incidence in infancy and childhood. *Staphylococcus aureus* causes several diseases, the most frequent and serious of which are bacteremia and its complications in hospitalized patients. In particular, *S. aureus* can cause wound infections and infections associated with catheters and prosthetic devices. Serious infections associated with *S. aureus* bacteremia include osteomyelitis, invasive endocarditis and septicemia. *Staphylococcus epidermidis* causes disease primarily in patients with impaired host defenses or altered microbial flora, and is common in newborns. In particular, *S. epidermidis* can cause urinary tract infections, infections associated with IV catheters, meningitis in patients with subacute bacterial endocarditis, and it can cause mastitis in dairy animals.

*Bacillus pumilus* strain Sh 18 ("*B. pumilus* Sh18") is a nonpathogenic, enteric, gram-positive bacterium. It has been reported that this bacterium produces a cell wall polysaccharide (sometimes referred to as a teichoic acid) that cross-reacts serologically with the capsular polysaccharide (CP) of Hib (Argman et al. (1974), *J Immunol*. 112, 649-55). This cross reactivity has been attributed to poly(ribotol phosphate) known to be present in cell wall associated teichoic acids of at least some bacilli (Kojima et al. (1985) *J. Bacteriol* 161, 299-306). No cross-reactivity, however, was observed with Hia CP, which is structurally similar to Hib CP, and which also contains ribotol phosphate in its subunit. It has been suggested that enteric, non-pathogenic gram positive bacteria, such as *B. pumilus* Sh18, may serve as a source of natural immunity against Hib in children over 6 years old and in adults (Bradshaw et al. (1971), *Lancet* 1095-6). Cross reactivity of *B. pumilus* Sh18 cell wall polysaccharide (CWP) with bacterial cell surface polysaccharides other than Hib has not been suggested or reported previously.

One aspect of the present invention is a vaccine comprising a glycoconjugate preparation containing polysaccharides from the *B. pumilus* Sh18 cell wall. This vaccine, surprisingly, cross reacts with surface polysaccharide material from all four of the pathogenic bacteria discussed above.

DESCRIPTION OF THE INVENTION

Figure 1:
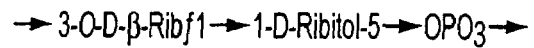
FIG. 1 shows structures of capsular polysaccharides (CP) and cell wall polysaccharides (CWP) that cross-react with *B. pumilus* Sh18 CWP.
Figure 1:
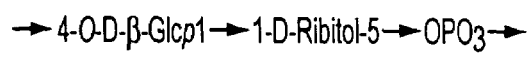
Figure 1:
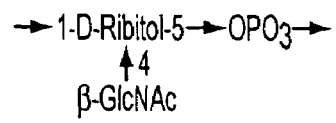
Figure 1:
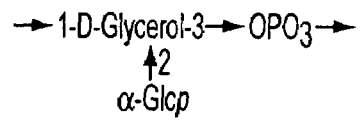
Figure 1:
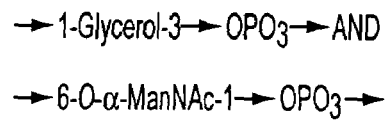
Figure 1:
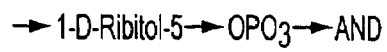
Figure 1:
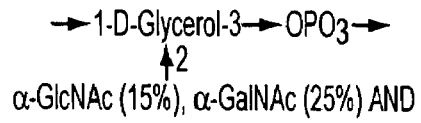
Figure 1:
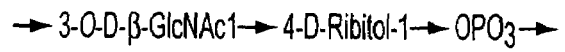

The present inventors have determined the structure of a cell wall polysaccharide ("CWP") composition from the enteric, gram positive, non-pathogenic bacterium, *Bacillus pumilus* Sh 18. The CWP composition comprises three polysaccharide (PS) components: (1) a major component which comprises a 1,5-poly(ribitol phosphate); (2) a major component which comprises 1,3-poly(glycerol phosphate) that is partially substituted by 2-acetamido-2-deoxy-α-galactose (about 14%) and 2-acetamido-2-deoxy-α-glucose (about 7%) on position C-2; and (3) a minor component which comprises a poly(2-acetamido-2-deoxy-β-glucosyl-1→4-ribitol phosphate) with the phosphodiester bonds located between C-1 of ribitol and C-3 of 2-acetamido-2-deoxy-β-glucose.

The CWP composition cross reacts with antisera prepared against both *Haemophilus influenza* type b (Hib) and *Staphylococcus epidermidis* (*S. epidermidis*), as well as antisera prepared against cell wall material from *B. pumilus* Sh 18 and from the closely related non-pathogenic bacterium, *B. pumilus* Sh 17.

Also disclosed are several types of glycoconjugate preparations which comprise components of the above *B. pumilus* Sh 18 cell wall polysaccharide composition. One of these glycoconjugate preparations is made by activating the terminal phosphate residues of the polysaccharides, e.g., with 1-ethyl-3-(3-dimethylaminopropyl)carbodiimide-HCl (EDAC), in order to facilitate their binding to a protein or peptide. Surprisingly, such a glycoconjugate preparation cross-reacts with a wide spectrum of sera prepared against bacterial capsular polysaccharides, including those from at least the four pathogenic bacteria: *Haemophilus influenza* type a (Hia), *Haemophilus influenza* type b (Hib), *Staphylococcus aureus* (*S. aureus*) and *Staphylococcus epidermidis* (*S. epidermidis*). The glycoconjugate preparation also reacts with sera prepared against the non-pathogenic bacteria, *B. pumilus* Sh18, itself, and against the closely related non-pathogenic bacterium, *B. pumilus* Sh17. Those reactivities with non-pathogenic bacteria are generally not referred to further in the present disclosure, but are to be understood to occur.

Such a glycoconjugate preparation, when introduced into a subject, can elicit an immunological response against at least the four above-mentioned pathogenic cross-reactive bacteria, and thus can serve, e.g., as a multiorganism vaccine. Advantages of such a multiorganism vaccine include, e.g., ease and simplicity of administration, greater patient compliance, and lower production costs than separate vaccines for each of the organisms. Among the classes of patients that would benefit from such a multiorganism vaccine are, e.g., immunocompromised patients, and patients from Africa or other countries in which infections with both Hia and others of the cross-reacting bacteria are prevalent.

Furthermore, such a glycoconjugate preparation can be used to elicit an antibody that can be used in methods of passive immunity. The antibody will react with at least the four above-mentioned pathogenic bacteria, and thus will exhibit advantages similar to those discussed above for the multivalent vaccine.

The present invention relates, e.g., to a glycoconjugate preparation (e.g., composition), comprising one or more polysaccharides from a cell wall polysaccharide preparation from *B. pumilus* Sh 18, wherein one or more of the polysaccharides is bound to a protein or peptide. Embodiments of this glycoconjugate preparation react with at least an antiserum generated against *S. epidermidis, H. influenza* type a (Hia), and/or *S. aureus*, and, optionally, with an antiserum generated against *H. influenza* type b (Hib). Preferably, the glycoconjugate preparation reacts with antisera generated against at least all four of those pathogenic bacteria. Furthermore, embodiments of this glycoconjugate preparation induce antibodies cross-reactive with at least cell wall polysaccharide (CWP) of *S. aureus* and/or *S. epidermidis* and/or with CP of Hia and, optionally, with CP of Hib. Preferably, the glycoconjugate preparation induces antibodies cross-reactive with at least CP or CWP of all four of those pathogenic bacteria.

In other embodiments of the invention, the glycoconjugate preparation comprises a poly(ribitol phosphate) (e.g., a 1,5-poly(ribitol phosphate)) and/or a poly(glycerol phosphate) (e.g., a 1,3-poly(glycerol phosphate)) and, optionally, a poly (2-acetamido-2-deoxy-β-glucosyl-1→4-ribitol phosphate) with the phosphodiester bonds located between C-1 of ribitol and C-3 of 2-acetamido-2-deoxy-β-glucose. In some embodiments, the 1,3-poly(glycerol phosphate) is partially substituted by 2-acetamido-2-deoxy-β-galactose and/or 2-acetamido-2-deoxy-α-glucose on position C-2, e.g., about 14% of the 1,3poly(glycerol phosphate) is substituted by 2-acetamido-2-deoxy-β-galactose, and/or about 7% is substituted by 2-acetamido-2-deoxy-α-glucose.

Another aspect of the invention is a glycoconjugate preparation that consists essentially of (a) a poly(ribitol phosphate) (e.g., an unsubstituted poly(ribitol phosphate), such as an unsubstituted 1,5-poly(ribitol phosphate)) or (b) a poly(glycerol phosphate) (e.g., an unsubstituted poly(glycerol phosphate), such as an unsubstituted 1,3-poly(glycerol phosphate)), wherein the polysaccharide (a) or (b) is bound to a protein or peptide.

Another aspect of the invention is a glycoconjugate preparation, which is not necessarily isolated from *B. pumilus* Sh 18 CWP, and which comprises one or more (preferably all three) of the following types of polysaccharides:

(a) a 1,5-poly(ribitol phosphate) (e.g., an unsubstituted 1,5-poly(ribitol phosphate));
(b) a 1,3-poly(glycerol phosphate (e.g., an unsubstituted or partially substituted 1,3-poly(glycerol phosphate)); or
(c) a poly(2-acetamido-2-deoxy-α-glucosyl-1→4-ribitol phosphate) with the phosphodiester bonds located between C-1 of ribitol and C-3 of 2-acetamido-2-deoxy-β-glucose. In one embodiment, the 1,3-poly(glycerol phosphate) is partially substituted on position C-2 by 2-acetamido-2-deoxy-β-galactose and/or 2-acetamido-2-deoxy-α-glucose, e.g., about 14% of the 1,3-poly (glycerol phosphate) is substituted by 2-acetamido-2-deoxy-β-galactose, and/or about 7% is substituted by 2-acetamido-2-deoxy-α-glucose. In one embodiment, the molar ratio of components (a), (b) and (c) is approximately 56:34:10. The precise ratio of the three components is not critical, and can vary somewhat depending on, e.g., growth conditions. Any ratio which provides a glycoconjugate having functional properties according to the invention (e.g., the ability to react with an antiserum generated against *S. epidermidis*, Hia, and/or *S. aureus*, and, optionally, Hib) is within the scope of the invention.

In the glycoconjugate preparations of the invention, one or more (e.g., all) of the polysaccharides may be bound to peptides or proteins by a linkage via a hydroxyl group of the polysaccharide. For example, the polysaccharide may be bound to the peptide or protein by a linkage via a terminal hydroxide group of the peptide or protein. When linkage via a hydroxyl group is present, the glycoconjugate generally reacts with an antiserum generated against at least *S. epidermidis*; and/or the glycoconjugate induces antibodies cross reactive with capsular polysaccharide (CP) of at least *S. epidermidis*.

Alternatively, one or more of the polysaccharides may be bound to peptides or proteins via a linkage between a terminal phosphate group of the polysaccharide and a reactive amino group of the peptide or protein. For example, the reactive amino group may be in an adipic dihydrazide (ADH) group that has been used to derivative the peptide or protein. When this type of linkage is present, the glycoconjugate generally reacts with antisera generated against at least *S. epidermidis*, Hia, and/or *S. aureus*, and, optionally, Hib (preferably against at least all four of those pathogenic bacteria); and/or the glycoconjugate induces antibodies cross reactive with at least cell wall polysaccharide (CWP) of *S. aureus* and/or *S. epidermidis* and/or with capsular polysaccharide (CP) of Hia and, optionally, with CP of Hib. Preferably, the glycoconjugate induces antibodies cross reactive with at least CWP or CP of all four of those pathogenic bacteria.

The glycoconjugtes of the invention are isolated glycoconjugates. As used herein, the term an "isolated" glycoconjugate refers to a glycoconjugate that is removed from its original environment (e.g., the natural environment if it is naturally occurring), and isolated or separated from at least one other component with which it is naturally associated. For example, a naturally-occurring glycoconjugate present in its natural living host is not isolated, but the same glycoconjugate, separated from some or all of the coexisting materials in the natural system, is isolated. Such a glycoconjugate could be part of a composition, and still be isolated in that such composition is not part of its natural environment.

The singular form "a," "an," and "the" includes plural referents unless the context clearly dictates otherwise. For example, "a" poly(ribitol phosphate) molecule as used above may refer to one or more poly(ribitol phosphate) molecules, e.g., one or more molecules of the same type (structure) of poly(ribitol phosphate), or one or more different types (structures) of poly(ribitol phosphate). "An" antibody refers to one or more antibodies, which may be the same or different.

Another aspect of the invention is a method for making a glycoconjugate preparation comprising at least one peptide or protein and at least one polysaccharide which contains a terminal phosphate group. The method comprises activating the terminal phosphate group of the polysaccharide, e.g. with 1-ethyl-3-(3 dimethylaminopropyl)carbodiimide-HCl (EDAC), and binding the activated phosphate group to a reactive amino group of the peptide or protein. For example, the reactive amino group may be in an adipic dihydrazide (ADH) group that has been used to derivatize the peptide or protein. This method may be used, for example, to make a glycoconjugate preparation as described above, e.g., using a polysaccharide preparation comprising polysaccharides from a CWP preparation from *B. pumilus* Sh 18, and/or using a polysaccharide composition comprising polysaccharide types (a), (b) and/or (c) as above. The method may be used to generate glycoprotein conjugates with any polysaccharide that contains a terminal phosphate group. This method of preparing a glycoconjugate may broaden the scope of cross-reactivities compared to that of a glycoconjugate made by other methods, which is an advantage of the method. The invention also relates to a glycoconjugate preparation made by this method.

Another aspect of the invention is glycoconjugate made with an isolated poly(glycerol phosphate) from the *B. pumilus* Sh18 cell wall polysaccharide. A skilled worker will be aware of conventional methods for isolating and, if desired, purifying, such a poly(glycerol phosphate). For example, the cell wall polysaccharide preparation can be oxidized to release the poly(glycerol phosphate) component, which can then be isolated from other components of the preparation. Alternatively, a poly(glycerol phosphate) can be generated synthetically, using conventional procedures. Such a synthetic poly(glycerol phosphate) is preferably unsubstituted. An unsubstituted polysaccharide would be expected to induce antibodies that are cross-reactive with poly(glycerol phosphate)-containing polysaccharides from a variety of bacteria, even if those bacteria contain poly(glycerol phosphate)-containing polysaccharides which are substituted with different substituents than the poly(glycerol phosphate)-containing polysaccharide of the *B. pumilus* Sh18 cell wall. Alternatively, the synthetic poly(glycerol phosphate) may be substituted, for example in the manner in which the poly(glycerol phosphate)-containing polysaccharide of the *B. pumilus* Sh18 cell wall is substituted.

Another aspect of the invention is a glycoconjugate made with an isolated poly(ribitol phosphate). Such a polysaccharide may be difficult to isolate from a *B. pumilus* Sh18 cell wall preparation; but it can be generated synthetically, using conventional procedures. See, e.g., Stadelmaier et al. (2003) *Angew Chem Int Ed Engl.* 42, 916-20; and Peeters et al. (1992) *Infect Immun.* 60, 1826-33. Preferably, the synthetic poly(ribitol phosphate) is unsubstituted. An unsubstituted polysaccharide would be expected to induce antibodies that are cross-reactive with poly(ribitol phosphate)-containing polysaccharides from a variety of bacteria, even if those bacteria contain partially or completely substituted poly(ribitol phosphate)-containing polysaccharides.

Preferably, a polysaccharide chain of the invention contains about 5-15 repeats of poly(ribitol phosphate) or poly(ribitol phosphate).

Methods of preparing glycoconjugates with the isolated poly(ribitol phosphate) or poly(ribitol phosphate) chains of the invention are conventional, as are methods to test whether a conjugate of interest elicits the desired specificity and/or degree of immunogenicity. One of skill in the art will recognize a variety of types of glycoconjugates that can be generated. For example, one can synthetically add a linker having an available amino group to a synthetic poly(ribitol phosphate) or poly(glycerol phosphate) chain, and conjugate this to a protein having an available carboxyl group, or vice versa. A wealth of suitable linker molecules will be evident to the skilled practitioner. Preferably, a glycoconjugate of the invention comprises about 5-20 polysaccharide chains per each protein or peptide molecule. For guidance in some synthetic methods of preparing conjugates, see Pozsgay et al. (1999) *Proc. Natl. Acad. Sci. USA* 96, 5194-5197; Schneerson et al, (2003) *Proc. Natl. Acad. Sci. USA* 100, 8945-8950.

Another aspect of the invention is an antibody or antibody preparation generated against a glycoconjugate preparation of the invention. Antibodies of the invention may be generated against glycoconjugates prepared with one or more naturally occurring polysaccharides (e.g., components of *B. pumilus* Sh18 CWP), or against active fragments or variants thereof, or against glycoconjugates prepared with synthetically generated polysaccharides.

In one embodiment, the antibody is a polyclonal antibody. A polyclonal antibody of the invention may be prepared against a glycoconjugate in which one or more of the polysaccharides are bound to peptides or proteins by a linkage via a terminal phosphate group of the polysaccharide. For example, the linkage may be formed by activating a terminal phosphate group of the polysaccharide (e.g., with EDAC) and then binding the activated phosphate to a reactive amino group in a suitable peptide or protein. A polyclonal antibody prepared in this manner preferably comprises species of antibody binding sites that react with polysaccharides of the cell walls of Hia, *S. aureus*, and/or *S. epidermidis* and, optionally, Hib (preferably against all four of those bacteria).

Alternatively, the polyclonal antibody may be prepared against a glycoconjugate in which one or more of the polysaccharides are bound to peptides or proteins by a linkage via a hydroxyl group of the polysaccharide. Preferably, the polyclonal antibody comprises species of antibody binding sites that react with polysaccharides of *S. epidermidis* (and/or *B. pumilus* Sh18 and/or Sh17), but not Hib, Hia, or *S. aureus*.

The invention also relates to an antibody preparation comprising a collection (mixture) of one or more monoclonal antibodies, which cross react with CP or CWP of Hia, *S. aureus*, and/or *S. epidermidis*, and, optionally, a monoclonal antibody specific for a cell wall polysaccharide of Hib. Preferably, the collection of monoclonal antibodies comprises species of antibody binding sites that react with CP or CWP of all four bacteria. The monoclonal antibodies can be generated, e.g., against a glyconjugate in which the linkage between the polysaccharide and the peptide or protein is via an activated phosphate group in the polysaccharide. Other suitable monoclonal antibodies can be generated against glycoconjugates made with isolated or purified poly(glycerol phosphate) or poly(ribitol phosphate).

The invention also relates to an antibody, either polyclonal or monoclonal, which is generated against a *B. pumilus* Sh18 CWP. Such an antibody preferably contains antibodies that react with the cell wall material of Hib and/or *S. epidermidis* (and/or *B. pumilus* Sh18 or Sh17), but does not contain antibodies that are cross-reactive with Hia, or *S. aureus*.

Another aspect of the invention is a pharmaceutical composition comprising a polyclonal antibody of the invention, or a collection of monoclonal antibodies of the invention, and a pharmaceutically acceptable carrier. Pharmaceutical compositions of the invention include compositions for therapeutic applications or for diagnostic uses.

Another aspect of the invention is a method for eliciting (inducing) an immune response in a subject, comprising administering to the subject an immunostimulatory-effective amount of a glycoconjugate preparation of the invention. The subject may be, e.g., a subject (e.g., a patient) who is likely to be exposed to (infected by), or who has already been exposed to (infected by), or is suspected of having been exposed to (infected by), Hia, *S. aureus*, and/or *S. epidermidis* and, optionally, Hib. In embodiments of the invention, the immune response is protective against infection by the bacteria Hia, *S. aureus*, and/or *S. epidermidis* and, optionally, Hib; in one embodiment, the immune response is protective against infection by all four of those bacteria. In one embodiment, the method further comprises detecting resistance of the subject to infection by Hia, *S. aureus*, and/or *S. epidermidis* and, optionally, Hib; in one embodiment, the method comprises detecting resistance of the subject to infection by all four of those bacteria.

Other aspects of the invention include an immunogenic composition that comprises a glycoconjugate preparation of the invention and a pharmaceutically acceptable carrier; and a vaccine that comprises a glycoconjugate preparation of the invention and, optionally, an adjuvant.

Other aspects of the invention are directed to immunotherapy methods. For example, the invention relates to an immunotherapy method, comprising administering to a subject in need thereof an effective amount of an antibody of the invention. Another embodiment of the invention is a hyperimmune globulin composition generated against a glycoconjugate preparation of the invention. The hyperimmune composition may comprise antibodies directed against cell wall components of Hia, *S. aureus*, and/or *S. epidermidis* and, optionally, Hib; or against cell wall components of all four of those bacteria. Another embodiment is a method for preparing an immunotherapy agent, comprising immunizing a subject with a glycoconjugate of the invention; collecting plasma from the immunized subject, and harvesting a hyperimmune globulin from the collected plasma. The hyperimmune globulin may contain antibodies directed against cell wall components of Hia, *S. aureus*, and/or *S. epidermidis* and, optionally, Hib; or against cell wall components of all four of those bacteria.

The present invention relates, e.g., to a glycoconjugate preparation, comprising a (one or more) polysaccharide(s) from a cell wall polysaccharide preparation from *B. pumilus* Sh 18, or a synthetically produced polysaccharide(s), bound to a peptide or protein. Such a glycoconjugate preparation can induce an immunological response when introduced into a subject, and is thus sometimes referred to herein as an "antigen."

Suitable polysaccharide constituents of the glycoconjugate preparations of the invention include any of the polysaccharides discussed herein. The polysaccharides may be isolated from a *B. pumilus* Sh 18, or from another suitable organism. Suitable methods for isolating and, optionally, purifying the polysaccharides are conventional. See, e.g., Schneerson et al. (1980), *J. Exp Med*, 152, 361-76, or Vann et al. (1976), *Infect Immun*. 13, 1654-62, or the present Examples. Depending on the growth conditions and the method of preparation, the glycoprotein composition may comprise varying proportions of the three polysaccharide types (a), (b), and (c) noted above; and the polysaccharides may exhibit different amounts and/or structures of the noted substituents, compared to the naturally occurring polysaccharides in the bacterium. Any such polysaccharide variant is in accordance with the invention, provided that it retains a functional property in accordance with the invention (e.g., the ability to react with an antiserum generated against *S. epidermidis*, Hia, and/or *S. aureus*, and, optionally, Hib). Alternatively, the polysaccharides may be generated synthetically, using procedures that will be evident to a skilled worker.

One or more (preferably all three) of polysaccharide types (a), (b) and (c) noted above may be used to generate a glycoconjugate preparation of the invention. Conventional methods may be used to separate (isolate) these three components, either partially or completely, e.g. if they are obtained from a *B. pumilus* Sh 18 cell wall preparation. Such a separation allows a glycoconjugate to be made with an individual polysaccharide component of interest. The Examples show, for example, that a component which reacts with antisera to *S. epidermidis* can be separated during immunoelectrophoresis from a component which reacts with anti-Hib antiserum.

Alternatively, antibodies of the invention can be used, in conjunction with other methods, for purifications of the individual antibodies, e.g., in immunoaffinity columns.

The polysaccharides may be of any length (size) that is effective to elicit an antigenic response. For example, a polysaccharide as small as about 3 kDa is likely to be antigenic. Generally, a mixture of the three polysaccharides, following isolation from *B. pumilus* Sh 18 by methods of the invention, is between about 10 and about 50 Kda. This size is suggested by the finding that the polysaccharide mixture elutes in the void volume of a Sephadex G50 column, and a bit after the void volume on a Sephadex G75 column.

The invention encompasses active fragments or active variants of the naturally occurring polysaccharides from *B. pumilus* cell wall. "Active fragments" can be of any suitable size, i.e., any size (and structure) that is capable of eliciting an immunological response that is substantially similar to the response against the naturally occurring, full length molecule. "Active variants" are variants which are capable of eliciting an immunological response that is substantially similar to the response against the naturally occurring, unmodified (non-variant) molecule. For example, polysaccharide components in which the substitutions are different from those found in the natural polysaccharide, or in which the substitutions are present in different amounts, may be suitable.

Any suitable peptide or protein may be used to make a glycoconjugate of the invention. The Examples illustrate the use of bovine serum albumin (BSA) or recombinant *Pseudomonas aeruginosa* exotoxin A (rEPA). Many other suitable proteins or peptides that can be used as immunocarriers will be known to the skilled worker, including, e.g., tetanus toxoid, diphtheria toxoid, or non-toxic mutant strains of EPA as described, for example, in Fattorn et al. (1993), *Inf. And Imm*. 61, 1023-1032. Conditions for optimizing the conjugation of a polysaccharide to a particular peptide or protein, such as varying the pH, are routine and conventional. Without wishing to be bound by any particular mechanism, it is suggested that such immunocarriers can improve the interaction between T and B cells, thereby enhancing the induction of an immune response against the antigen, which is particularly important for use in patients with reduced resistance. An immunocarrier can enhance immunogenicity both for active immunization and for preparing high-titered antisera in volunteers for passive immunization. Again without wishing to be bound by any particular mechanism, it is suggested that certain immunocarriers, or immunocarriers conjugated to a polysaccharide by a particular reactive group, can also broaden the range of targets to which an antiserum is antigenic. Such a broadening is illustrated in the Examples herein.

Glycoconjugates of the invention can be prepared by any of a variety of conventional methods. Some methods involve linkages via a hydroxyl group, such as a terminal hydroxyl, of the polysaccharide, e.g., they involve activating a polysaccharide by introducing a terminal ester group. For example, one can introduce terminal aldehyde groups into a polysaccharide via oxidative cleavage of vicinal diols, and then can couple the aldehyde groups to the peptide amino groups by reductive amination, as described, e.g., in U.S. Pat. No. 4,356,170. Alternatively, one can conjugate a polysaccharide to a peptide or protein by using any of a variety of known linking methods, such as an adipic dihydrazide (ADH) spacer, as described by Schneerson et al. (1980) *J. Exp. Med*. 1952, 361-476 and U.S. Pat. No. 4,644,059, or by binary spacer technology as described by Marburg et al. (1986) *J. Am. Che, Soc*. 108, 5282-5287. A variety of other conventional linkers will be known to the skilled worker, including synthetic linkers. Of course, any spacer molecule may be initially attached to one of the moieties as a derivative thereof, and then linked to the second moiety.

Another method is to activate hydroxyl groups of polysaccharides with cyanogen bromide and to react them with proteins that have been derivatized with adipic dihydrazide ADH (see, e.g., Shafer et al. (2000), *Vaccine* 18, 1273-81). Alternatively, the activated PS can react with cystamine and bind to proteins derivatized with N-succinimidyl-3-(2-pyridyldithio) proprionate (a SPDP-protein) (see, e.g., Fattom et al. (1992) *Infect Immun.* 60, 584-589).

The present Examples illustrate one method of making a glycoconjugate via a hydroxyl group ("Method 2"), in which the hydroxyl groups of the PS are activated with 1-cyano-4-dimethylaminopyridinium tetrafluoroborate (CDAP) and then incubated with a protein that has been derivatized with adipic dihydrazide (ADH). The Examples show that a glycoconjugate of the invention that is prepared by this method is useful, e.g., for generating an antibody which reacts with a cell wall polysaccharide of *S. epidermidis*.

The present inventors have devised a new method for making glycoconjugates, which can be carried out with any polysaccharide that contains a terminal phosphate group. In this method ("Method 1" in the Examples), the terminal phosphate group of the polysaccharide is activated, e.g., with 1-ethyl-3-(3-dimethylaminopropyl)carbodiimide-HCl (EDAC), and then incubated with a protein that has been treated with EDAC to activate its carboxyl groups and subsequently derivatized with ADH. Potentially, proteins with naturally occurring amino groups, such as, e.g., $\epsilon$-amino groups in lysine residues; amino groups in amino acid side chains that are longer than the side chain of lysine, in variants of lysine, or in synthetic molecules, or the like, can be used directly, instead of providing the reactive amino groups through an ADH derivative. A variety of linker molecules may also be used, using conventional procedures.

As the Examples show, a glycoconjugate comprising a polysaccharide from a cell wall polysaccharide preparation from *B. pumilus* Sh 18, when prepared by the preceding method, exhibits much broader cross-reactivity than does a glycoconjugate made by the more conventional methods. A glycoconjugate made by conventional methods (e.g., Method 2) elicits antibodies that cross-react with *S. epidermidis*, but not with Hia, Hib, or *S. aureus*. By contrast, a glycoconjugate made by the new method described herein (Method 1) can elicit antibodies that react with at least all four of those bacteria. The fact that the glycoconjugate cross reacts with these particular, disparate, bacteria is unexpected and advantageous.

A glycoconjugate of the invention, then, contains one or more (preferably all three) of the polysaccharide types (a), (b) and (c) described above, e.g., a polysaccharide isolated from a cell wall polysaccharide preparation from *B. pumilus* Sh 18, or a fragment or variant thereof, or a synthetic preparation thereof. The polysaccharides are bound to a peptide or protein. In one embodiment, the polysaccharide is bound to the peptide or protein by a linkage via a hydroxyl group of the polysaccharide. In another embodiment, the polysaccharide is bound to the peptide or protein by a linkage of a phosphate group of the polysaccharide to a reactive amino group of a peptide or protein. In one embodiment of the invention, the phosphate is a terminal phosphate of the polysaccharide; the amino group is part of an ADH derivative group, or an $\epsilon$-amino group of a lysine; and the conjugation is mediated by activation of the phosphate group with EDAC.

Another aspect of the invention is an antibody preparation generated against an antigenic composition of the invention (e.g., against a polysaccharide, or, preferably, against a glycoconjugate, of the invention).

Any of a variety of antibodies are included in the invention. Such antibodies include, e.g., polyclonal, monoclonal, recombinant, humanized or partially humanized, single chain, Fab, and fragments thereof, etc. The antibodies can be of any isotype, e.g., IgG, various IgG isotypes such as $IgG_1$, $IgG_{2a}$, etc.; and they can be from any animal species that produces antibodies, including goat, rabbit, mouse, chicken or the like. In one embodiment, Fab molecules are expressed and assembled in a genetically transformed host like *E. coli*. A lambda vector system is available thus to express a population of Fab's with a potential diversity equal to or exceeding that of subject generating the predecessor antibody. See Huse et al. (1989), *Science* 246, 1275-81.

In one embodiment, the antibody preparation is a polyclonal antibody preparation. In another embodiment, the antibody preparation comprises a collection (mixture) of one or more monoclonal antibodies (e.g., mouse or human monoclonals). This preparation comprises species of antibody binding sites that react with polysaccharides of the cell walls of Hia, *S. aureus*, and/or *S. epidermidis* and, optionally, Hib (preferably against all four of those bacteria). Protocols for producing these antibodies are conventional and are described, e.g., in Ausubel, et al. (eds.), Molecular Cloning: A Laboratory Manual, Cold Spring Harbor Laboratory, Cold Spring Harbor, N.Y.), Chapter 11; Bartal et al. (eds.), Methods of Hybridoma Formation, Humana Press, Clifton, N.J. (1988), pages 257-271; Vitetta et al. (1982), *Immunol. Rev.* 62, 159-83; and Raso (1982), *Immunol. Rev.* 62, 93-117.

An inoculum for polyclonal antibody production typically is prepared by dispersing a polysaccharide or glycoconjugate of the invention in a physiologically-tolerable diluent such as saline, to form an aqueous composition. Preferably, the inoculum comprises glyconjugates comprising each of the three *B. pumilus* Sh18 polysaccharide types described herein. However, the inoculum may also comprise a glycoconjugate having only one of those polysaccharides; or the inoculum may comprise one or more polysaccharides that are not in the form of a glycoconjugate.

An immunostimulatory amount of inoculum, with or without adjuvant, is administered to an animal, such as a mammal, and the inoculated mammal is then maintained for a time period sufficient for the antigen to induce antibodies. Antibodies can include antibody preparations from a variety of commonly used animals, e.g., goats, primates, donkeys, swine, rabbits, horses, hens, guinea pigs, rats, and mice, and even human antibodies after appropriate selection, fractionation and purification. Animal antisera may also be raised by inoculating the animals with formalin-killed *B. pumilus* Sh 18, by conventional methods, bleeding the animals and recovering serum or plasma for further processing.

The induced polyclonal antibodies can be harvested and isolated to the extent desired by well known techniques, such as by alcohol fractionation and column chromatography, or by immunoaffinity chromatography. Typical immunoaffinity chromatography includes binding an antigen to a chromatographic column packing like Sephadex™, passing the antiserum through the column, thereby retaining specific antibodies and separating out other immunoglobulins (IgGs) and contaminants, and then recovering purified antibodies by elution with a chaotropic agent, optionally followed by further purification, for example, by passage through a column of bound blood group antigens or other non-pathogen species. This procedure is preferred when isolating desired antibodies from the sera or plasma of humans that have developed an antibody titer against the pathogen(s) in question, thus assuring the retention of antibodies that are capable of binding to the antigen. They can then be used, e.g., in preparations for passive immunization against one or more of the bacteria noted above.

A monoclonal antibody (mAb) composition of the invention contains, within detectable limits, only one species of antibody combining site capable of effectively binding an epitope of a cell surface polysaccharide of one of the four bacteria noted above. Some monoclonal antibodies may be specific for an epitope that is common to all four of the cross-reacting polysaccharide types (e.g., a portion of a particular poly(ribitol phosphate)). Other monoclonal antibodies may be specific for an epitope that is present in only one of, or in two or three of, the cross-reacting polysaccharides. For example, a mAb produced in response to a poly(glycerol phosphate) of a *B. pumilus* Sh 18 cell wall polysaccharide may be specific for *S. epidermidis* (and for *B. pumilus* Sh18 and Sh 17), but not for bacteria whose cell wall components lack poly(glycerol phosphate), such as Hib, Hia and *S. aureus*. It is well within the ability of a skilled worker to determine the specificity of any mAb generated by a method of the invention, using conventional procedures. Various combinations of mAbs may be combined to produce a desired mixture (collection) of mAbs.

Suitable antibodies in monoclonal form can be prepared using conventional hybridoma technology. To form hybridomas from which a monoclonal antibody composition of the present invention is produced, a myeloma or other self-perpetuating cell line is fused with lymphocytes obtained from peripheral blood, lymph nodes or the spleen of a mammal hyperimmunized with a *B. pumilus* Sh 18 cell wall PS composition of the invention or, preferably, with a glycoconjugate of the invention. It is preferred that the myeloma cell line be from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA.

A Balb/C mouse spleen, human peripheral blood, lymph nodes or splenocytes are the preferred materials for use in preparing murine or human hybridomas. Suitable mouse myelomas for use in the present invention include the hypoxanthine-aminopterin-thymidine-sensitive (HAT) cell lines, a preferred myeloma being P3X63-Ag8.653. A suitable fusion partner for human monoclonal antibody production is SHM-D33, a heteromyeloma available from ATCC, Manassas, Va. under the designation CRL 1668.

A monoclonal hybridoma culture comprising a nutrient medium containing a hybridoma that secretes antibody molecules of the appropriate specificity is maintained under conditions and for a time period sufficient for the hybridoma to secrete the antibody molecules into the medium. The antibody-containing medium is then collected. The antibody molecules then can be isolated further by well known techniques.

Media useful for the preparation of these compositions are well known in the art and commercially available, and include synthetic culture media, inbred mice, or the like. An exemplary synthetic medium is Dulbecco's Minimal essential medium supplemented with 20% fetal calf serum. An exemplary inbred mouse strain is the Balb/C.

Other methods of preparing monoclonal antibody compositions are also contemplated, such as interspecies fusions, since it is primarily the antigen specificity of the antibodies that affects their utility in the present invention. Human lymphocytes obtained from infected individuals can be fused with a human myeloma cell line to produce hybridomas which can be screened for the production of antibodies that recognize the antigen(s) noted above. More preferable in this regard, however, is a process that does not entail the use of a biological sample from an infected human subject. For example, a subject immunized with a vaccine as described herein can serve as a source for antibodies suitably used in an antibody composition within the present invention.

Monoclonal antibodies of the invention can be partially or fully humanized, using conventional procedures. For example, humanized monoclonal antibodies can be produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al. (1989), *Proc. Nat'l Acad. Sci. USA* 86, 3833 (1989). Techniques for producing humanized monoclonal antibodies are described, for example, in U.S. Pat. No. 6,054,297; Jones et al. (1986), *Nature* 321, 522 (1986); Riechmann et al. (1988), *Nature* 332, 323; Verhoeyen et al. (1988), *Science* 239, 1534; Carter et al. (1992), *Proc. Nat'l Acad. Sci. USA* 89, 4285; Sandhu (1992), *Crit. Rev. Biotech.* 12, 437 (1992); and Singer et al. (1993), *J. Immunol.* 150, 2844. Transgenic mouse strains are available for the generation of fully humanized antibodies.

If desired, antibodies of the invention can be linked together to further increase their anti-multiorganism specificity. Such multivalent antibodies can be polyspecific for two or more of the bacterial polysaccharides discussed herein, or for other antigens. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods for preparing such hybrid antibody fragments are conventional and are disclosed, e.g., in Feteanu, Labeled Antibodies in Biology and Medicine, McGraw-Hill Int'l Book Co. (1978), 321 23; Nisonoff, et al. (1961), *Arch Biochem. Biophys.* 93, 470; Hammerling, et al. (1968), *J. Exp. Med.* 128, 1461; and U.S. Pat. No. 4,331,647.

Other methods are known in the art to make bivalent fragments that are entirely heterospecific, e.g., the use of bifunctional linkers to join cleaved fragments. Recombinant molecules are known that incorporate the light and heavy chains of an antibody, e.g., according to the method of Boss et al., U.S. Pat. No. 4,816,397. Analogous methods of producing recombinant or synthetic binding molecules having the characteristics of antibodies are included in the present invention. More than two different monospecific antibodies or antibody fragments can be linked using various linkers known in the art. See, also, methods discussed in U.S. patent application 2002/0025317.

In one embodiment of the invention, a monoclonal or polyclonal antibody directed against a *B. pumilus* Sh18 CWP antigen (polysaccharide or, preferably, glycoconjugate) is used as a pharmaceutical preparation in an imunotherapy method, e.g., in a therapeutic or prophylactic application. Such a method can confer passive immunity from a host individual to another individual (e.g., augment an individual's immune response against one of the bacterial discussed herein, or provide a response in an immuno-compromised or immuno-depleted individual). Passive transfer of antibodies is known in the art and may be accomplished by any of the known methods. According to one method, antibodies directed against a *B. pumilus* Sh18 CWP or a conjugate thereof of this invention are generated in an immunocompetent host ("donor") animal, harvested from the host animal, optionally purified (e.g., by affinity purification) and transfered to (e.g., transfused into) a recipient individual. For example, a human donor may be used to generate antibodies reactive against a PS or glycoconjugate of this invention. The antibodies may then be administered in therapeutically or prophylactically effective amounts to a human recipient in need of treatment, thereby conferring resistance in the recipient against bacteria that are bound by antibodies elicited by the polysaccharide component. (See, e.g., Grossman et al. in "Basic and Clinical Immunology", 7th Ed., (Stites, D. P. and Terr, A. T. eds., Appleton & Lange 1991) Chapter 58 "Immunization").

Similarly, monoclonal or polyclonal antibodies produced according to the present invention can be conjugated to an immunotoxin, and administered to a subject in whom the infection has already occurred but has not become widely spread. To this end, antibody material produced pursuant to the present description would be administered in a pharmaceutically acceptable carrier, as defined herein.

The invention includes antibodies generated against the noted bacteria, which are protective or non-protective. A non-protective antibody can have a variety of utilities, including, e.g., use as a reagent for detecting the presence of an antigen. For example, non-protective antibodies can be used in diagnostic methods, or in experimental studies to elucidate the structure of bacterial cell wall components.

Among the diagnostic assays that can be performed with antibody preparations of the invention are screening assays. For example, antibodies can be used for screening a group of fresh bacterial isolates to distinguish between those which contain ribitol phosphate and those which contain glycerol phosphate as a subunit of their surface antigens. In this case, either ribitol phosphate or glycerol phosphate would be used as a group antigen. Similar assays are used for streptococcal group antigens.

Another aspect of the invention is a method for eliciting (inducing) an immune response in a subject (e.g., a patient), comprising administering to the subject an immunostimulatory effective amount of a polysaccharide or glycoconjugate of the invention. By an "immunostimulatory effective amount" is meant herein an amount effective to induce a detectable amount of an immune response. The term, an "immune response," as used herein, includes the induction of any of the types of antibodies described elsewhere herein. The immune response can be a protective response against, e.g., a bacterium having a cross-reacting antigen, or it can be non-protective. An immune response can also be the induction of cellular immunity.

Suitable subjects (e.g., patients in need of such treatment) include any animal that can generate an immune response, such as, e.g., mammals, including cat, mouse, rat, rabbit, guinea pig, hen, goat, donkey, burro, pig, horse, cow, non-human primate or, preferably, a human. For example, a suitable patient would be one who is likely to be exposed to (infected by), or who has already been exposed to (infected by), or who is suspected of having been exposed to (infected by), Hia, *S. aureus*, and/or *S. epidermidis* and, optionally, Hib. Conditions that can be prevented or treated by a method of the invention include any condition mediated by infection by one of the above-mentioned bacteria, including, e.g., the conditions discussed in the Background Information section above.

In some embodiments of the invention, the immune response is protective against infection by at least one of (or as many as all four of) the bacteria described herein. Thus, a *B. pumilus* Sh 18 cell wall CWP preparation or a glycoconjugate of the invention can be used as a component of a vaccine. A vaccine that is protective against two or more of these bacteria is sometimes referred to herein as a "multivalent," "polyvalent," or "antimultiorganism" vaccine.

Methods of determining if an immunogenic composition of the invention can serve as a protective vaccine are conventional. For example, one can inoculate a mammalian subject to create bacteremia and challenge the inoculated animal with one or more of the bacteria discussed herein. However, the induction of bacteremia in mammals requires extremely high numbers of organisms or some previous maneuver to lower the host resistance.

Alternatively, in vitro phagocytosis, can be studied as a correlate of protective immunity in vivo. In this model, the ability of a *B. pumilus* Sh 18-specific monoclonal or polyclonal antibody to opsonize in vitro *B. pumilus* Sh 18, and/or any of the four pathogenic bacteria discussed herein, is measured by phagocytosis, using conventional methods (e.g., the method described in Kojima et al. (1990), *Infect. Dis. Immun.* 58, 2367-2374). Antibodies induced by a *B. pumilus* Sh18 antigen vaccine facilitate type-specific phagocytosis. The in vitro phagocytosis assays thus indicate that antibodies to the *B. pumilus* Sh18 antigen are protective against infection by *B. pumilus*, or any of the bacteria discussed herein that carry the antigen.

Pursuant to the present invention, a vaccine can be administered to a subject not already infected with one or more of the noted bacteria, thereby inducing a protective immune response (humoral or cellular) in that subject. Alternatively, a vaccine within the present invention can be administered to a subject in which infection by one or more of these bacteria already has occurred but is at a sufficiently early stage that the immune response produced to the vaccine effectively inhibits further spread of infection.

In another approach, a vaccine of the present invention can be administered to a subject who then acts as a source for globulin, produced in response to challenge from the specific vaccine ("hyperimmune globulin"), that contains antibodies directed against one or more of the noted bacteria. A subject thus treated would donate plasma from which hyperimmune globulin would then be obtained, via conventional plasma-fractionation methodology, and administered to another subject in order to impart resistance against or to treat infection by the bacteria. Hyperimmune globulins according to the invention are particularly useful for immune-compromised individuals, for individuals undergoing invasive procedures or where time does not permit the individual to produce his own antibodies in response to vaccination.

A *B. pumilus* Sh 18 antigen (polysaccharide or glycoconjugate) or antibody of the invention can be the active ingredient in a pharmaceutical composition, which further comprises a pharmaceutically acceptable carrier for the active ingredient. The pharmaceutical composition can be used, e.g., in a therapeutic or prophylactic application to confer passive immunity, or as a vaccine to induce a cellular immune response and/or production in vivo of antibodies which combat these bacterial infections. In this regard, a pharmaceutically acceptable carrier is a material that can be used as a vehicle for administering a medicament because the material is inert or otherwise medically acceptable, as well as compatible with the active agent, e.g., in the context of vaccine administration. Typical pharmaceutically acceptable carriers include, e.g., physiological saline, dextrose, glycerol, ethanol, or other injectable liquids. Additives customary in vaccines may also be present, for example stabilizers such as lactose or sorbitol, and adjuvants to enhance the immunogenic response such as aluminum phosphate, hydroxide, or sulphate and stearyl tyrosine. Other agents, such as antioxidants, preservatives, or solubilizing agents, may also be present.

Preferably, an antigen (polysaccharide or glycoconjugate) is administered without an adjuvant in order to avoid adjuvant-induced toxicity. If an adjuvant is used, it may be one that promotes the protective $IgG_2$ antibodies. Typical adjuvants include complete Freund's adjuvant (CFA) and incomplete Freund's adjuvant (IFA). Dextran sulfate has been shown to be a potent stimulator of $IgG_2$ antibody against staphylococcal cell surface antigens, and also is suitable as an adjuvant.

The pharmaceutical compositions of this invention may be introduced to an individual by methods known to be effective in the art. Intradermal, intraperitoneal, intravenous, subcutaneous, intramuscular, oral and intranasal are among, but not the only, routes of administration.

Pharmaceutical compositions (including vaccines) of the present invention are administered in amounts sufficient to elicit production of antibodies as part of an immunogenic response. Dosages may be adjusted based on the size, weight or age of the individual receiving the pharmaceutical composition. The antibody response in an individual can be monitored by assaying for antibody titer or bactericidal activity and boosted if necessary to enhance the response. Typically, a single dose vaccine for an infant is about 10 µg of conjugate vaccine per dose or about 0.5 µg-20 pg/kilogram. Adults generally receive a vaccine dose of about 0.5 µg-20 µg/kilogram of the conjugate vaccine.

In the foregoing and in the following examples, all temperatures are set forth in uncorrected degrees Celsius; and, unless otherwise indicated, all parts and percentages are by weight.

EXAMPLES

Example I

Materials and Methods

A. Bacterial Strains

The following bacterial strains were used in this study: *Bacillus pumilus* Sh 18 and Sh 17 (Meyrowitz et al. (1973), *Infect Immun.* 8, 896-900); *Heamophilus influenzae* type b (Eagan and Rab); *Heamophilus influenzae* type a strain Harding; *Staphylococcus aureus* type 5 strain Lowenstein; and *Staphylococcus epidermidis* RP-62A (ATCC 35981). *Bacillus pumilus* Sh 18 was obtained from the ATCC collection.

*B. pumilus* Sh 18 and Sh 17 were cultured in the ultrafiltrate of Tryptic Soy Broth (TSB), *H. influenzae* type a and b as previously reported (Schneerson et al., (1980), *J Exp Med.* 152, 361-76), *S. aureus* as described (Fattom et al. (1990), *Infect Immun.* 58, 2367-74), and *S. epidermidis* on chemically-defined medium (Hassain et al, (1991), *J. Med Microbiol* 34, 143-47).

B. Cell Wall Polysaccharide

Capsular polysaccharides (CP) from *H. influenzae* types a and b, and cell wall polysaccharides (CWP) from *S. aureus* and *B. pumilus* Sh18 and Sh17 were prepared as described in Schneerson et al. (1980), *J. Exp Med,* 152, 361-76 and Vann et al. (1976), *Infect Immun.* 13, 1654-62). Briefly, CP and CWP were isolated from culture supernatant by precipitation with 0.1% Cetavlon and purified by enzyme treatment and cold phenol extraction, followed by separation on a Sepharose CL-6B gel filtration column (0.2 M NaCl as eluent). The identity of *H. influenzae* types a and b CP was confirmed by precipitation in double immunodiffusion with the type specific burro serum against *H. influenzae* types a and b (Myerowitz et al. (1973), *Infect Immun,* 8, 896-900) and by nuclear magnetic resonance (NMR) spectroscopy by comparison to the published spectra (Lemercinier et al. (2000) *Biologicals* 28, 175-183; Zon et al. (1983) *Carbohydr. Res.* 114, 103-121. The CWP of *S. aureus* type 5 was further separated from its CP by Sephadex DEAE chromatography. Fractions showing a positive reaction with rabbit anti-*S. aureus* teichoic acid serum and a negative reaction with rabbit anti-*S. aureus* type 5 CP were collected. *S. epidermidis* CWP was precipitated with 80% ethanol from culture supernatant, treated with enzymes and chromatographed on a BioGel P100 column equilibrated with PBS. Anti-*S. epidermidis* sera were prepared by intravenous immunization of rabbits with acetone-dried bacterial cells as described (Alexander et al. (1946) *J Immunol* 54, 207-214). *B. pumilus* Sh18 CWP was further purified by passage through Sephadex DEAE chromatography (0.1-2.0 M NaCl gradient). Fractions demonstrating positive reactions with *H. influenzae* type b antiserum were collected and analyzed.

C. Analytical Determination

Sugar analysis was carried out according to Sawardeker et al, (1965), *Anal. Chem.* 37, 1602-1604. In brief, 0.5 mg of each PS was hydrolyzed in 48% HF for 1 h at 60° C. in plastic tubes (Ip et al. (1992), *Anal Biochem.* 201, 343-9), and/or in 10 M HCl for 30 min in 80° C. and, after reduction and peracetylation, analyzed by GLC-MS using a Hewlett-Packard apparatus (model HP 6890) with a type HP-5 glass capillary column (0.32 mm by 30 m) and temperature programming at 8° C./min, from 125-250° C. in the electron ionization (106 eV) mode. Ribitol was distinguished from ribose by performing the reduction step with sodium bromodeuteride. Amino acid analysis was carried out by GLC-MS after hydrolysis with 6 N HCl at 150° C. for 1 h and derivatization to volatile N-heptafluorobutyryl isobutyl esters of amino acids (MacKenzie (1987), *J. Assoc. Off. Anal. Chem,* 70, 151-160) and muramic acid after trimethylsilyl derivitization (Bal et al. (2002) *J Microbiol Methods* 48, 267-270), using the same GLC-MS apparatus and temperature program as above. Protein concentration was assayed by the Lowry method; phosphate content was determined according to the method of Chen et al. (1956) *Anal Chem* 28, 1756-1758; and the amount of hydrazide groups was determined in a 2,4,6-trinitrobenzene sulfonic acid (TNBS) assay.

D. Hydrofluoric Acid Treatment and Methylation Analysis

Sh18 CWP (15 mg) was treated with 1 ml of aqueous 48% HF at 4° C. for 48 h in plastic tubes. HF was evaporated under nitrogen and the hydrolyzed components were separated on a BioGel P2 column equilibrated with water. Separated fractions were lyophilized and analyzed. Fraction F2 was subjected to methylation analysis: 2 mg were methylated as described (Ciucanu et al. (1984) *Carbohydr. Res.* 131, 209-217), hydrolyzed, converted to alditol acetates and analyzed by GLC-MS (Sawardeker et al. (1965) *Anal. Chem.* 37, 1602-1604.

E. Periodate Oxidation

Sh18 CWP (15 mg) were treated with 1 ml of 0.1M $NaIO_4$ at 4° C. for 48 h in the dark. Excess periodate was then destroyed by the addition of 0.2 ml of ethylene glycol, followed by the addition of 20 mg of sodium borohydride. After 15 h at 4° C., the solution was desalted on a prepacked PD10 column (Pharmacia), applied to a BioGel P60 column equilibrated with 20 mM ammonium bicarbonate, and connected to a Uvicord SII detector ($A_{206}$ and $A_{280}$).

F. Mild Acid Hydrolysis

Sh18 CWP was treated with 10 mM HCl for 10 min at 100° C. as described (Kojima et al. (1985), *Eur J. Biochem*, 149, 331-336). Acid was evaporated under nitrogen and the material was applied to a BioGel P60 column equilibrated with 20 mM ammonium bicarbonate and connected to a Uvicord SII detector ($A_{206}$ and $A_{280}$).

G. Fast Atom Bombardment (FAB)-MS

Mass spectra were recorded by using a JEOL SX102a magnetic sector instrument with xenon and 6 keV atoms to ionize samples from 3-nitrobenzyl alcohol or glycerol matrix.

H. NMR Spectroscopy

NMR spectra were acquired at 300 K, by use of a Bruker DRX-500 spectrometer with either a 5 mm HCN TXI probe, or a 5 mm broadband BBO probe. Solutions of 5-13 mg of compound in $D_2O$ (99.96 atom % D) were used for analysis, with acetone as a reference at 2.225 ppm and 31.0 ppm, respectively, for $^1H$ and $^{13}C$ NMR. In most cases, 32,768-point data sets were used for 1D spectra, in some instances with zero-filling or complex, forward linear predictions to 32,768, 65,536 or 131,072 points. 1D $^1H$ NMR spectra were recorded at 500 MHz with a spectral width of 3.21 or 4.25 kHz, a 30° pulse (2.7 or 3.2 μs), and a recycle time of 6 s. 1D $^{13}C$ NMR spectra were acquired at 126 MHz using a spectral width of 25.1 kHz, a 45° or 90° pulse (6 μs), a recycle time of 0.653, 1 or 2 s, and WALTZ-16 $^1H$ decoupling. Methylene $^{13}C$ resonances were identified by the DEPT method, using a 135° $^1H$ read pulse. $^1H$ coupled $^{13}C$ NMR spectra were acquired with the NOE by use of gated, WALTZ-16 irradiation at the $^1H$ frequency. 1D $^{31}P$ NMR spectra were recorded at 202 MHz by using 16,384-point data sets, a spectral width of 6.07 kHz, a 90° pulse (8 μs), a recycle time of 4.85 s, continuous, WALTZ-16 $^1H$ decoupling at 500 MHz, and 85% $H_3PO_4$ containing 10% $D_2O$ as an external reference at −0.73 ppm. $^1H$ coupled 1D $^{31}P$ NMR spectra were acquired without the NOE.

2D correlation spectroscopy (COSY) $^1H$ NMR spectra were collected in 2048×512-point data sets, zero-filled to 2048×2048 points. Unshifted sine-bell squared window functions were applied in both dimensions prior to Fourier transformation, after which the frequency data were displayed in magnitude mode. 2D total COSY (TOCSY) $^1H$ NMR spectra were acquired using 16384×256 point data sets, zero-filled to 16384×2048 points, by use of the z-gradient-selected (GS), phase sensitive, echo/anti-echo protocol. 1D $^1H$ NMR subspectra of individual residues were produced by extraction of $F_2$ slices from the 2D TOCSY spectra. For further confirmation of assignments, some 2D TOCSY experiments were conducted with either selective, digital, homonuclear $^1H$ decoupling, or continuous, WALTZ-16 $^{31}P$ decoupling. 2D HSQC and HMBC $^1H/^{13}C$ NMR spectra were recorded as 2048×512 or 800 point data sets, zero-filled to 2048×2048 points, using the gs, sensitivity-enhanced, phase-sensitive echo/anti-echo mode for HSQC, and a gs, low-pass filtered, long-range, non-decoupled pulse sequence for HMBC, the data from which were displayed in magnitude mode. 2D HMBC NMR spectra were acquired with an evolution delay of 83 ms, i.e., optimized for $^{2,3}J_{CH}$ 6.0 Hz. 2D $^1H/^{31}P$ HMBC was conducted at 500/202 MHz by using a long-range enhanced, non-decoupled pulse sequence with 8192 ($F_2$)× 512 ($F_1$) point data sets, optimized for $^{2,3}J_{HP}$ 6 Hz, and with $F_1$ processing in the magnitude mode.

2D $^1H/^{13}C$ and $^1H/^{31}P$ HSQC-TOCSY experiments were performed at 500/126 MHz and 500/202 MHz, respectively, by the gs sensitivity-enhanced method with the echo/antiecho protocol, together with 2048 or 4096 points ($F_2$)×800 points ($F_1$), GARP $^{13}C$ or $^{31}P$ decoupling during acquisition, respectively, and a TOCSY MLEV mixing time of 140 ms. The phase-sensitive, $^1H/^{13}C$ experiment was optimized for $^1J_{CH}$ 145 Hz, whereas the $^1H/^{31}P$ method was optimal for $^{2,3}J_{PH}$ 6 Hz, with $F_1$ ($^{31}P$) processing in the magnitude mode. Resolution enhancement of 1D and 2D NMR spectra was performed either by Gaussian multiplication using a line-broadening of −0.75 to −5 Hz and a Gaussian broadening fraction of 0.3, by a sine-bell squared window function shifted by either zero or π/3 rad to π/10 rad, or by complex, forward linear prediction to 2-4 times the raw data size in $F_2$ and 2-8 times the raw data size in $F_1$.

I. Conjugation of Sh 18 CWP

Method 1.

Step I: Bovine serum albumin (BSA, Sigma) was derivatized with adipic dihydrazide (ADH), as described in Schneerson et al. (1980), *J. Exp Med* 152 (2), 361-76.

Step II: BSA-AH was mixed with Sh18 CWP at a concentration of 10 mg/ml (each). The pH was adjusted to 5.8 with 0.1M HCl, and 1-ethyl-3-(3 dimethylaminopropyl)carbodiimide-HCl (EDAC) was added to a concentration of 0.1M. The reaction was continued at room temperature for 4 h at pH 5.8. The solution was dialyzed overnight against saline at 4° C. and applied to a Sephadex CL-6B column (1×100 cm) equilibrated in 0.2 M NaCl. Fractions showing an identity line with anti-BSA and anti-Hib by double immunodiffusion were collected; and protein and phosphate concentrations were measured.

Method 2.

Step I: Recombinant *Pseudomonas aeruginosa* exotoxin A (rEPA) was purified as described (Blumentals et al. (1987), *Appl Environ Microbiol* 53, 2013-20) and derivatized with ADH as above.

Step II: the Sh18 CWP was reacted with 1-cyano-4-dimethylaminopyridinium tetrafluoroborate (CDAP) as reported (Shafer et al. (2000), *Vaccine* 18, 1273-81) to form a cyanate ester derivative (CWP-O—C≡EN). Sh18 CWP (10 mg) was dissolved in water at 5 mg/ml, the pH was adjusted to 9.0, and a solution of 10 mg of CDAP in 0.1 ml of acetonitryl was added. After 30 sec of mixing, 100 ul of 0.2 M triethylamine was added, followed by 10 mg of rEPA-AH in 0.6 ml of PBS over the next 2.5 min. The pH was maintained at 8.0-8.5 for 3 h, and the solution was left at 4° C. overnight. The solution was dialyzed overnight against saline at 4° C. and applied to a Sepharose CL-6B column as described above. Fractions showing an identity line with anti-*P. aeruginosa* endotoxin A (List Biological Lab., Inc.) and anti-Hib antibodies were collected; the protein and phosphate contents were assayed.

J. Immunization and Immunological Assays

Groups of 10 5- to 6-week-old female NIH general-purpose mice were injected subcutaneously three times, 2 weeks apart, with 2.5 ug of Sh18 CWP as a conjugate Mice were exsanguinated 1 week after the last injection, and sera were stored at −20° C.

The levels of antibodies were evaluated by ELISA using CovaLink plates (Nunc). In this assay, the terminal phosphate group of polysaccharide, in the presence of carbodiimide, forms a phosphoramide bond with secondary amino group exposed on the surface of the wells. Plates were coated with CP of *H. influenzae* types a and b and *E. coli* (negative control), and CWP of *B. pumilus* Sh 18 and Sh17, *S. aureus* type 5 and *S. epidermidis* RP-62A. Polysaccharides (5 µg/ml) were dissolved in 10 mM 1-methylimidazol buffer (pH 7), and EDAC was added to a final concentration of 50 mM. The antigens were applied at 100 µl per well and incubated at 37° C. overnight. Plates were washed 6 times with 0.1% Brij 35-saline and blocked with 1% HSA in PBS for 1 h at room temperature. Twofold dilutions of the sera were made in 1% HSA-0.1% Brij 35-saline and incubated at 37° C. for 4 h. Plates were washed, goat anti-mouse immunoglobulin G (IgG) conjugated to alkaline phosphatase were added and incubated at 37° C. for 3 h. 4-nitrophenylphosphate (1 mg/ml in 1M Tris hydrochloride buffer, pH 9.8) and containing 0.3 mM $MgSO_4$) was added, and the $A_{405}$ was read after 30 min in an MR600 microplate reader (Dynatech). Some ELISAs were run using the avidin-biotin system. Murine monoclonal anti-Hib antibodies (0.52 mg/ml) were used as a standard for the ELISA. An inhibition ELISA was done by incubating mouse sera induced by Sh18 CWP conjugate I, diluted to the concentration that gave an $A_{405}$ absorption of 1.0, with 5 or 20 µg of Hib, Hia, *E. coli* KI and *E. coli* K93 CP or Sh18, *S. aureus*, and *S. epidermidis* CWP/ml for 1 h at 37° C. and overnight at 4° C. The assay was then continued as above. Sera with and without inhibitor, at the same dilution, were compared. Percent inhibition was defined as follows: [1-($A_{405}$ of adsorbed serum)/($A_{405}$ of nonadsorbed serum)]× 100%.

Bactericidal activity of the was assayed using precolostral calf serum as a source of complement and Hib strain Eagan and Hia strain Harding.

Double immunodiffusion, rocket and intermediate gel immunoelectrophoresis, and quantitative precipitation assays were done as described (Handbook of Immunoprecipitation-in-Gel Techniques, Axelsen N H (editor) (1983); *Scand J Immunol*, 10 (17), 57-70, and 103-112; Kabat et al. (1961), In C. C. Thomas, Editor, *Experimental Immunochemistry*, Thomas, Springfield, 22-96).

Absorption of burro and anti-Hib serum with Sh18-CWP was done by adding 1 mg of CWP to 20 ml of serum (the ratio was based on the maximum precipitation in the quantitative precipitation assay). The solution was incubated at 37° C. for 1 h and at 4° C. for 2 days. The precipitate was removed by centrifugation at 37,000×g for 10 min and washed, and the composition was analyzed for ribitol and glycerol contents by GLC-MS.

Example II

Isolation and Characterization of *B. pumilus* Sh 18 CWP

Figure 2:
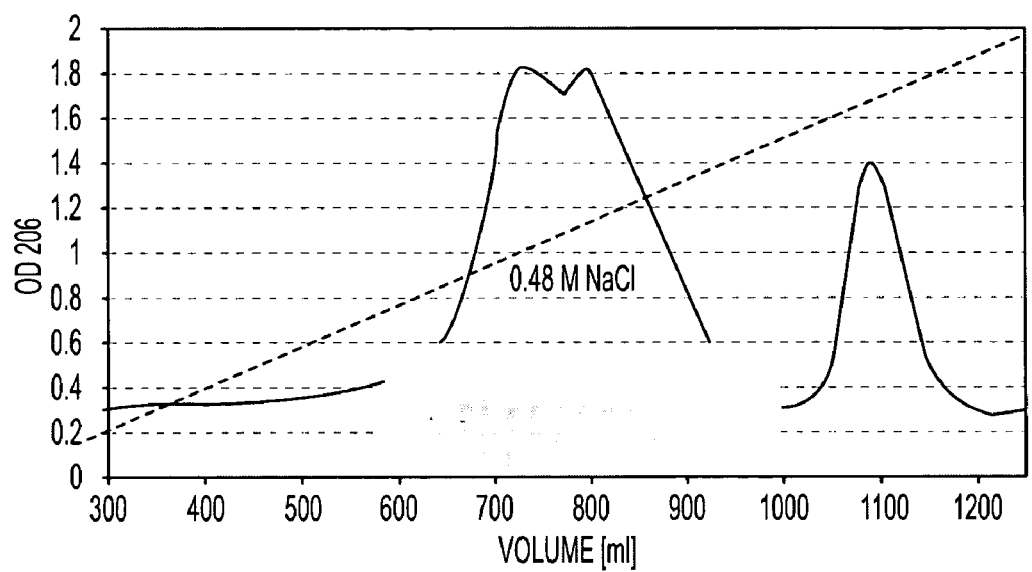
FIG. 2 shows chromatography of *B. pumilus* Sh 18 CWP on a Sepharose DEAE ion-exchange column and rocket immunoelectrophoresis of the eluted fractions with anti-*H. influenzae* type b serum.

*B. pumilus* Sh18 CWP was eluted from a Sepharose CL-6B column with a $K_d$ of 0.5 and from a Sephadex DEAE column by 0.48 M NaCl. In both cases, the CWP showed size and charge heterogeneity. The use of other sizing columns did not separate this peak into more components. This peak was divided into 5 fractions and compositional analysis of the eluted fractions showed that each contained ribitol, glycerol, and amino sugars, but in different molar ratios. The peak from the DEAE-Sephadex column that reacted with anti-Hib serum (FIG. 2), designated as Sh 18-CWP, was further characterized.

GLC-MS analysis of Sh18 CWP detected peracetylated derivatives of glycerol, ribitol, glyucosamine, and galactosamine (Table 1), and the CWP contained 10.7 wt % of phosphorous. HF hydrolysis (48% HF, 1 hat 60° C.) released only ribitol and glycerol, whereas additional hydrolysis with HCl released amino sugars, indicating that they are bound by glycosidic linkages.

TABLE 1

Molar ratio of *B. pumilus* Sh18 CWP components and the compositions of fractions obtained after HF and sodium periodate degradation as determined by GLC-MS. GlcNAc: 2-acetamido-2-deoxy-glucose; GalNAc: 2-acetamido-2-deoxy-galactose

| Sample preparation | Molar ratio of | | | |
|---|---|---|---|---|
| | Glycerol | Ribitol | GlcNAc | GalNAc |
| Sh18-CWP[1] | 0.43 | 1.0 | 0.0 | 0.0 |
| Sh18-CWP[2] | 0.45 | 1.0 | 0.15 | 0.06 |
| Sh18-HF-1[3] (11%) | 0.0 | 0.0 | 1.0[4] | 0.0 |
| Sh18-HF-2 (57%) | 0.6 | 1.0 | 0.7 | 0.30 |
| Sh18-HF-3 (32%) | 0.2 | 1.0 | 0.0 | 0.0 |
| Sh18-oxid-1 | 1.0 | 0.0 | 0.08 | 0.0 |
| Sh18-oxid-2 | 1.0 | 0.0 | 0.7 | 0.0 |

Figure 3:
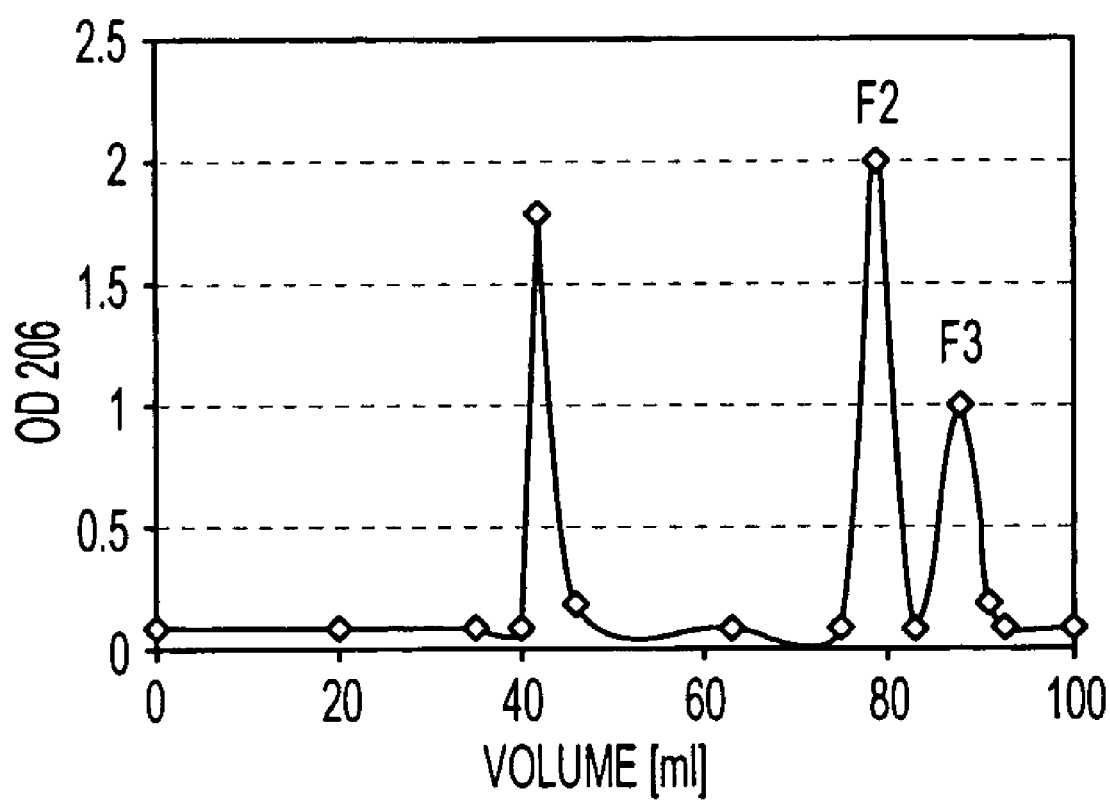
FIG. 3 shows chromatography of HF-digested *B. pumilus* Sh 18 CWP on a BioGel P-2 column.

[1]hydrolysis with HF,
[2]hydrolysis with HF followed by HCl,
[3]hydrolysis with HF followed by fractionation on a Bio Gel P-2 column,
[4]Sh18 HF-1 fraction also contained traces of muramic acid and amino acids detected in separate experiments by GLC-MS Treatment of the Sh18 CWP with HF (48%, 4° C. for 48 h) followed by BioGel P-2 chromatography revealed low-molecular-mass components (FIG. 3). These components were subjected to GLC-MS (Table 1). The first fraction (Sh18HF-1) contained glucosamine and small amounts of alanine, glutamic and diaminopimelic and muramic acid, suggesting the presence of cell wall fragments. The second fraction (Sh18HF-2) contained disaccharides: 2-acetamido-2-deoxy-hexosylribitol (pseudomolecular ion $[M-1]^+$ of 356) and 2-acetamido-2-deoxy-hexosylglycerol (pseudomolecular ion $[M-1]^+$ of 296) as determined by FAB-MS analysis. GLC-MS analysis revealed peracetylated glycerol, ribitol, 2-acetamido-2-deoxy-galactose and 2-acetamido-2-deoxy-glucose in the molar ratio presented in Table 1. Methylation analysis performed with GLC-MS detected 4-O-acetyl-1,2,3,5-tetra-O-methyl-ribitol and 1,5-di-O-acetyl-2,3,4,6-tetra-O-methyl-2-N-methylacetamido-2-deoxy-glucitol as major components, indicating the substitution of ribitol by GlcNAc on carbon C-4. Free ribitol and glycerol were recovered in fraction Sh18HF-3.

Figure 4:
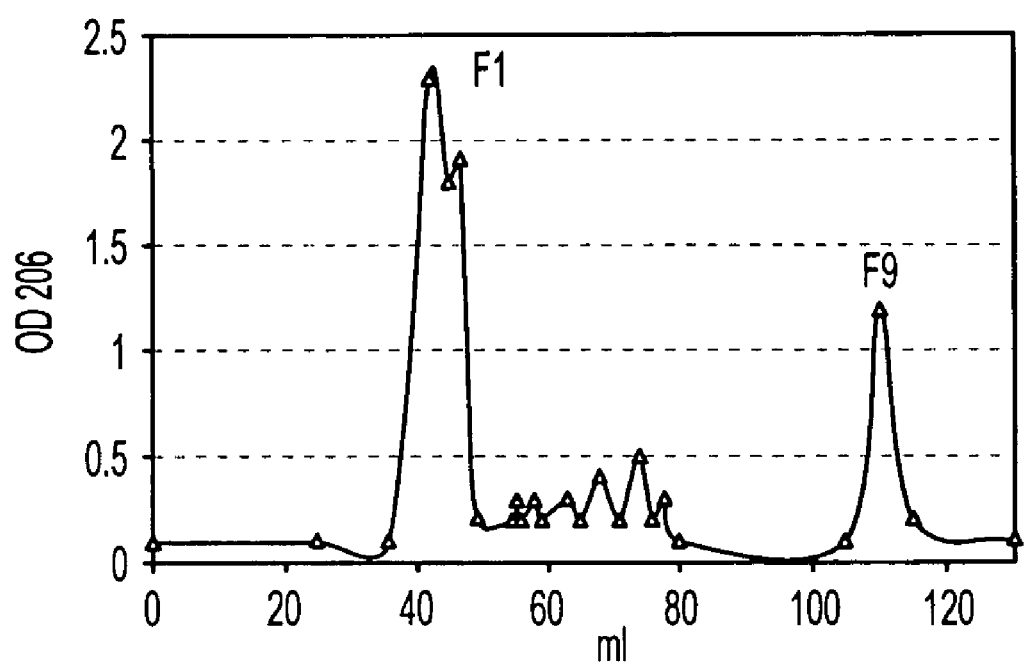
FIG. 4 shows chromatography of oxidized *B. pumilus* Sh 18 CWP on a BioGel P-60 column.

In the next step, oxidation of the Sh18 CWP with periodate was performed, and the products were separated on a BioGel P-60 column and analyzed (FIG. 4). No ribitol was detected, indicating that it had been completely oxidized. The composition of the two major fractions eluted from the column (Sh18-oxid-1, Sh18-oxid-2) is shown in Table 1. GLC-MS and NMR analysis of Sh18-oxid-1 demonstrated the presence of 1,3-poly(glycerol phosphate). The low-molecular-mass fraction Sh18-oxid-2 was composed of glycerol and β-GlcNAc phosphate, representing the degradation products of the minor polymer: ->3-O-β-GlcNAc-(1->4)-ribitol-1-$OPO_3$.

In order to examine whether the polymers were bound to each other by the cell wall fragments, the Sh18 CWP was treated with 10 mM HCl, as mild acid hydrolysis has been reported to cause cleavage of the linkage between the cell wall polysaccharide and the phosphate on the muramic acid in the peptidoglycan moiety (Argman et al. (1985) *J Bacteriol* 161, 299-306). The product of mild acid hydrolysis was eluted from a BioGel P60 column as a single peak, in the same position as the nontreated material, indicating that it was not affected by this treatment. GLC-MS analysis revealed ribitol, glycerol, and amino sugars in molar ratios similar to those of the original material; also, NMR analysis revealed a similar spectrum.

Example III

Immunological Properties

Sh18-CWP reacted by double immunodiffusion with anti-Hib and anti-*S. epidermidis* antibodies with a strong precipitation line and showed a weaker line with anti-*S. aureus* teichoic acid serum. Immunoelectrophoresis with the intermediate gel containing anti-Hib and the upper gel containing anti-*S. epidermidis* serum showed that part of the CWP was captured by the anti-Hib, whereas some migrated further and precipitated with the anti-*S. epidermidis* serum. Similar results were obtained when the order of the antisera in the gels was reversed. These data suggest that at least some of the poly(glycerol phosphate) and poly(ribitol phosphate) chains of Sh18-CWP were not bound. To further address the question of possible linkage between the polymers, Sh18 CWP was precipitated with anti-Hib serum, and the resulting precipitate was washed and analyzed by GLC-MS. The analysis revealed glycerol, ribitol and glucosamine in the ratio: 0.2:1.0:0.1. Without wishing to be bound by any particular type of association, the lesser amount of glycerol than in the original preparation might indicate that some of the poly(glycerol phosphate) may have been free and some may have been connected to the poly(ribitol phosphate). In any case, the precise fashion by which polysaccharides of the invention are associated with one another and/or with proteins or peptides in a glycoconjugate of the invention is presently not viewed as critical.

Example IV

NMR Analysis

*B. pumilus* Sh 18 CWP NMR spectrum showed characteristic shifts for poly(ribitol phosphate) and poly(glycerol phosphate) as compared to standards (Table 2). The ratio of ribitol carbons to those of glycerol was close to 1:0.5.

TABLE 2

$^{13}$C and $^{31}$P NMR chemical shifts (ppm) of polysaccharides and their fragments from *B. pumilus* Sh18, *S. epidermidis*, and *S. aureus*.

| | | *B. pumilus* Sh18 | F2/HF | F3/HF | *S. epidermidis* | *S. aureus* |
|---|---|---|---|---|---|---|
| Rib-P[a] | C-1 | 67.24d | | | | 65.65d |
| | C-2 | 71.62d | | | | 71.00d |
| | C-3 | 71.93 | | | | 71.75 |
| | C-4 | 71.62d | | | | 80.19d |
| | C-5 | 67.24d | | | | 67.41d |
| Gro-P | C-1 | 67.02d | | | 66.06d | |
| | C-2 | 70.35t | | | 76.14t | |
| | C-3 | 67.02d | | | 65.34d | |
| Rib | C-1 | | | 63.15 | | |
| | C-2 | | | 72.87 | | |
| | C-3 | | | 72.97 | | |
| | C-4 | | | 72.87 | | |
| | C-5 | | | 63.15 | | |
| β-GlcNAc | C-1 | 101.63 | 102.00 | | | 102.12 |
| | C-2 | 55.59d | 56.49 | | | 56.43 |
| | C-3 | 79.53d | 74.52 | | | 74.64 |
| | C-4 | 70.36d | 70.59 | | | 70.66 |
| | C-5 | 75.94 | 76.50 | | | 76.50 |
| | C-6 | 61.35 | 61.38 | | | 61.38 |
| | NAc | 23.36 | 23.01 | | | 23.20 |
| | C=O | 175.54 | 175.53 | | | 175.76 |
| α-GalNAc | C-1 | 97.76 | 97.88 | | | |
| | C-2 | 50.52 | 50.75 | | | |
| | C-3 | 68.46 | 68.39 | | | |
| | C-4 | 69.34 | 69.26 | | | |
| | C-5 | 71.85 | 71.95 | | | |
| | C-6 | 61.98 | 61.95 | | | |
| | NAc | 22.84 | 22.71 | | | |
| | C=O | 175.34 | 175.38 | | | |
| α-GlcNAc | C-1 | 97.60 | 97.66 | | | |
| | C-2 | 54.42 | 54.53 | | | |
| | C-3 | 71.65 | 71.65 | | | |
| | C-4 | 70.82 | 70.70 | | | |
| | C-5 | 72.83 | 72.90 | | | |
| | C-6 | 62.22 | 61.26 | | | |
| | NAc | 22.86 | 22.63 | | | |
| | C=O | 175.35 | 175.21 | | | |
| α-Glc | C-1 | | | | 98.50 | |
| | C-2 | | | | 72.25 | |
| | C-3 | | | | 73.72 | |
| | C-4 | | | | 73.42 | |
| | C-5 | | | | 72.60 | |
| | C-6 | | | | 61.33 | |
| β-GlcNAc-Rib | C-1 | 67.24d | 62.97 | | | |
| | C-2 | 70.85d | 71.95 | | | |
| | C-3 | 71.5 | 72.17 | | | |
| | C-4 | 82.42 | 82.59 | | | |
| | C-5 | 62.24 | 61.59 | | | |

TABLE 2-continued $^{13}$C and $^{31}$P NMR chemical shifts (ppm) of polysaccharides and their fragments from
B. pumilus Sh18, S. epidermidis, and S. aureus.

|  |  | B. pumilus Sh18 | F2/HF | F3/HF | S. epidermidis | S. aureus |
|---|---|---|---|---|---|---|
| α-GalNAc-Gro | C-1 | 66.05d | 62.09 |  |  |  |
|  | C-2 | 76.40t | 79.77 |  |  |  |
|  | C-3 | 66.05d | 61.14 |  |  |  |
| α-GlcNAc-Gro | C-1 | 65.24d | 62.11 |  |  |  |
|  | C-2 | 76.46t | 79.81 |  |  |  |
|  | C-3 | 64.24d | 62.14 |  |  |  |
| Rib-P | P-1(5) | 3.64 | 3.00 |  |  | 3.24 |
| Gro-P | P-1(3) | 3.08 | 3.00 |  |  | 2.45 |
| β-GlcNAc-P | P-3 | 2.59 |  |  |  |  |
| α-GalNAc-Gro-P | P-1(3) | 2.84 |  |  |  |  |
| α-GlcNAc-Gro-P | P-1(3) | 2.84 |  |  |  |  |

<sup>a</sup>The suffix P indicates the attachment of a phosphate group to the polyol or amino sugar.,
nr - not resolved
Table 2. $^1$H-NMR chemical shifts of polysaccharides and their fragments from B. pumilus Sh18, S. epidermis and S. aureus.

For a more extensive summary of NMR analyses, see Kubler-Kielb et al. (2004) *J Bacteriology* 186, 6891-6901.

Example V

Characterization of Cross-Reactive Polysaccharides

The identity and purity of *H. influenzae* type a and b CP was evaluated by NMR spectroscopy by comparison of the isolated polysaccharides with the published spectra (Zon et al. (1983), *Carbohydr Res.* 114, 103-21; Lemercinier et al. (2000), *Biologicals* 28, 175-83; Branefors-Helander (1977), *Carbohydr Res.* 56, 117-22). GLC-MS and NMR data obtained for other cell wall polysaccharides of Gram (+) bacteria demonstrated that *S. aureus* polysaccharide was composed of 1,5-poly(ribitol phosphate) substituted with 2-acetamido-2-deoxy-β-glucose on C-2 and *S. epidermidis* polysaccharide of 1,3-poly(glycerol phosphate) substituted with α-glucose on C-2. CWP from *B. pumilus* Sh17 was a mixture of unsubstituted 1,3-poly(glycerol phosphate) and 1,6-poly(2-acetamido-2-deoxy-α-mannose phosphate) in the molar ratio 1:0.4. These data are in agreement with previous reports (Baddily et al. (1962), *Biochem J.* 82, 439-448; Endl et al. (1984), *Arch Microbiol.* 137, 272-80; Vann et al. (1976), *Infect Immun.* 13, 1654-62). The structures are presented on FIG. 1 and $^{13}$C NMR shifts in Table 2.

Example VI

Conjugate Preparation and Immunological Studies

Two types of Sh18 conjugates were prepared:
Conjugate I (made by Method 1): BSA-AH-(EDAC)-Sh18 CWP, in which the EDAC-activated terminal phosphate group of the CWP was bound to ADH-derivatized protein; and
Conjugate II (made by Method 2): rEPA-AH-(CDAP)-CWP, in which CDAP-activated hydroxyl groups of the CWP were bound to ADH-derivatized protein.

Figure 5:
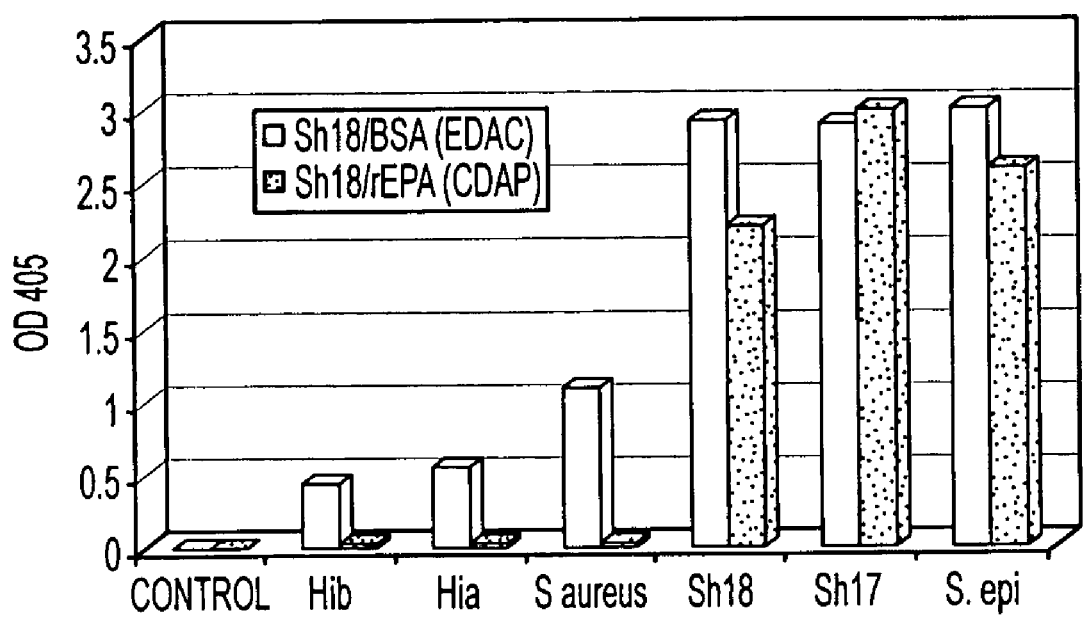
FIG. 5 shows an ELISA of antiserum against a *B. pumilus* Sh 18 CWP-protein conjugate on a plate coated with different polysaccharides.
Figure 6:
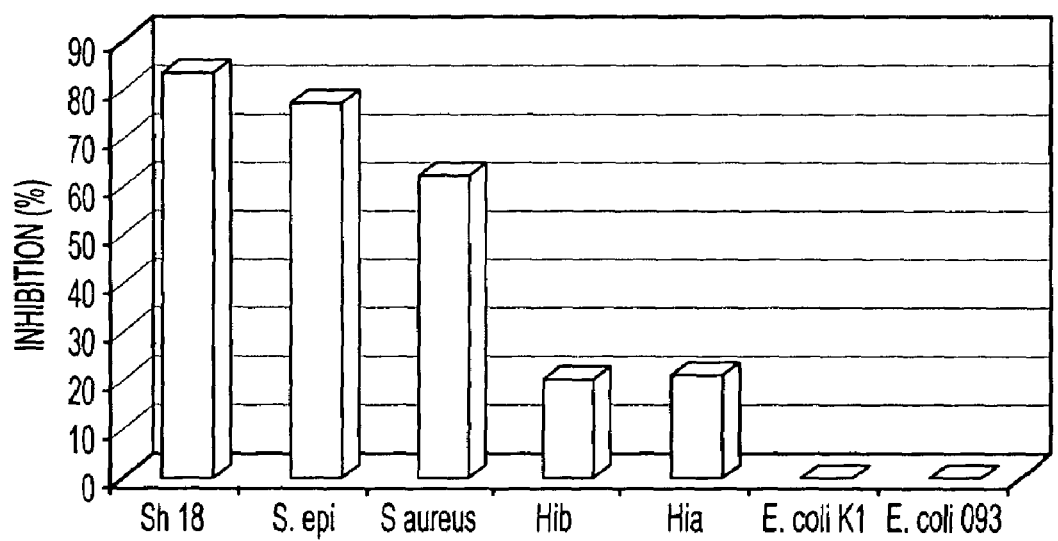
FIG. 6 shows the inhibition of an anti-*B. pumilus* Sh 18 CWP-BSA conjugate with different polysaccharides.

The protein/CWP weight ratios in conjugate I and conjugate II were 2.5:1.0 and 2.7:1.0, respectively. The ratios of glycerol, ribitol, GlcNAc and GalNAc, measured by GLC-MS, were 0.45:1.0:0.25:0.11 and 0.50:1.0:0.12:0.08, respectively. $^{31}$P NMR analyses of the conjugates showed similar spectra to those of native CWP. Double immunodiffusion analysis of both showed a line of identity with antiI-Hib and anti-protein sera. Antibody levels induced by the conjugates and the inhibition by cross-reactive polysaccharides are presented in FIG. 5 and FIG. 6. Conjugate I-induced antibodies reacted with ribitol phosphate-containing polysaccharides of Hib, Hia, and *S. aureus* and with glycerol phosphate-containing polysaccharides of Sh18, Sh17 and *S. epidermidis*, whereas conjugate II-induced antibodies reacted only with polysaccharides containing glycerol phosphate. No bactericidal activity against Hib and Hia was detected in sera induced by the conjugates diluted 1:4. Quantitative analysis of these sera assayed in comparison with a monoclonal anti-Hib serum showed levels of anti-Hib antibodies of about 1.0 µg/ml.

Antibody levels measured for polysaccharides covalently bound between the terminal phosphate group and the secondary amino groups on the surface of the CovaLink plates or by the avidin-biotin system were similar. An advantage of using CovaLink plates was that the technique was simple and did not required previous derivatization of hydroxyl groups of the polysaccharides with ADH.

Without wishing to be bound by any particular mechanism, it is suggested that the fact that CDAP reacts mainly with hydroxyl groups of ribitol may explain the loss of inimunogenicity of the ribitol phosphate in Sh18 CWP. The activation of terminal phosphate with EDAC and binding it to ADH-derivatized protein is preferred for constructing conjugates that exhibit broad cross-reactivity.

Example VI

Demonstration of Protective Immunity

A. In Vitro Opsonophagocytosis Assays
Polymorphonuclear leukocytes (PMNs) are obtained from suitable cells, such as HL-60 cells, and adjusted to a concentration of about $1.0 \times 10^7$ cells per ml in a suitable culture medium (e.g., MEM supplemented with 10% fetal bovine serum (FBS)). *B. pumilus* Sh 18, or one of the cross-reacting bacteria, is grown overnight in a suitable growth medium. The concentration of bacteria is adjusted spectrophotometrically to a suitable concentration (e.g., to an OD of about 0.02 at 540 nm ($4 \times 10^6$ cells/ml)), then adjusted to about $1 \times 10^6$ cells/ml in the culture medium in which the bacteria were grown. Purified antigen-specific or control non-reactive IgGs are added to facilitate opsonization by PMNs. Suitable controls will be evident to the skilled worker. For example, complement, such as baby rabbit complement, diluted to an appropriate dilution, such as 1:8, in the culture medium, may be used.

The reaction mixture contains about 25 µl the bacterial preparation (concentration 1.×10⁶ cells/ml), about 25 µl PMNs (concentration 1×10⁷ cells/ml), about 25 µl complement, about 100 µl sera or antibodies, and sufficient culture medium (e.g., MEM/10% FBS) to bring the total reaction volume to 250 µl. At 0 hours, 1 hours and 2 hours, 25 µl of sample are serially diluted. 25 µl of the $10^{-2}$, $10^{-3}$, $10^{-4}$ and $10^{-5}$ dilutions are plated onto suitable plates (e.g., TSA agar plates), and incubated overnight at 37° C.

The results are expected to show that antibody to the glycoconjugate mediates opsonophagocytosis of a bacterium that carries the cross-reacting antigen. The results are reported as percent killing by amounts of antigen-specific IgG in a suitable range (e.g., ranging from about 300 µg to about 128 µg). For comparison, percent killing by an equivalent amount of non-reactive IgG is also determined. PMNs plus complement is used as a control.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and below and in the figures are hereby incorporated by reference.

REFERENCES

Argaman et al. (1974), *J. Immunol.* 112, 649-655; Myerowitz et al. (1973), *Infection and Immunity* 7, 137-140; Zielen et al. (1996), *J. Immunol Methods.* 1931-7; Archibald et al. (1966), *Adv Carbohydr Chem Biochem.* 21, 323-75; Naumova et al. (1997), *Biochemistry* (Mosc). 62, 809-40; Sutton et al. (1985), *J Immunol Methods* 82, 215; U.S. Pat. Nos. 6,194,101; 6,248,570; and 4,711,779.

We claim:

1. A glycoconjugate preparation comprising
   (a) an unsubstituted 1,5-poly(ribitol phosphate);
   (b) a 1,3-poly(glycerol phosphate); and
   (c) a poly(2-acetamido-2-deoxy-β-glucosyl-1→4-ribitol phosphate) with the phosphodiester bonds located between C-1 of ribitol and C-3 of 2-acetamido-2-deoxy-β-glucose,
   wherein one or more of the polysaccharides is bound to a protein or a peptide.

2. The glycoconjugate of claim 1,
   wherein about 14% of the 1,3-poly(glycerol phosphate) is substituted by 2-acetamido-2-deoxy-β-galactose, and/or about 7% is substituted by 2-acetamido-2-deoxy-α-glucose, on position C-2.

3. The glycoconjugate of claim 1,
   wherein the molar ratio of (a), (b) and (c) is approximately 56:34:10.

4. The glycoconjugate preparation of claim 1, wherein one or more of the polysaccharide(s) are bound to peptides or proteins by a linkage of a terminal phosphate group of the polysaccharide to a reactive amino group of the peptide or protein.

5. The glycoconjugate preparation of claim 4, wherein the reactive amino group is in an adipic dihydrazide (ADH) derivative group on the peptide or protein.

* * * * *